United States Patent [19]

Janssen et al.

[11] Patent Number: 5,587,387

[45] Date of Patent: Dec. 24, 1996

[54] HETEROCYCLE-SUBSTITUTED BENZENEMETHANAMINE DERIVATIVES

[75] Inventors: Marcel A. C. Janssen, Vosselaar; Georges H. P. Van Daele, Turnhout; Jean-Paul R. M. A. Bosmans, Edegem; Marc G. C. Verdonck, Gierle; Paul A. J. Janssen, Vosselaar, all of Belgium

[73] Assignee: Janssen Pharmaceutica N.V., Beerse, Belgium

[21] Appl. No.: 432,748

[22] Filed: May 2, 1995

Related U.S. Application Data

[63] Continuation-in-part of Ser. No. 240,737, filed as PCT/EP92/02993, Dec. 22, 1992, published as WO93/13069, Jul. 8, 1993, Pat. No. 5,480,997.

[30] Foreign Application Priority Data

Dec. 30, 1991 [EP] European Pat. Off. ............ 91203431

[51] Int. Cl.$^6$ ................. A61K 31/47; C07D 215/38; C07D 215/22; C07D 215/20

[52] U.S. Cl. .................. 514/312; 514/313; 546/157; 546/159; 546/162; 546/112; 546/287; 546/288; 546/289; 546/296; 546/297; 546/307; 546/309; 546/310

[58] Field of Search ................... 546/112, 287, 546/288, 289, 296, 297, 307, 309, 310, 157, 159, 162; 514/312, 313

[56] References Cited

U.S. PATENT DOCUMENTS

| | | | |
|---|---|---|---|
| 4,246,429 | 1/1981 | Janssen et al. | 562/456 |
| 5,480,997 | 1/1996 | Janssen et al. | 546/289 |

*Primary Examiner*—Alan L. Rotman
*Attorney, Agent, or Firm*—Charles J. Metz

[57] ABSTRACT

The present invention is concerned with antiretroviral (e.g. anti-HIV-1)compounds having the formula

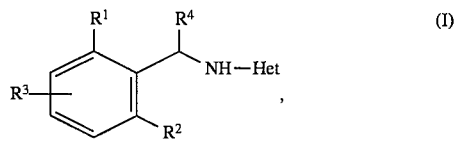

wherein $R^1$ and $R^2$ each independently are halo or methyl; $R^3$ is hydrogen, halo, nitro or trifluoromethyl; $R^4$ is trifluoromethyl or methylcarbonyl; or a radical —C(=X)—$NR^5R^6$ wherein X is O or S, and $R^5$ and $R^6$ each independently are hydrogen or $C_{1-4}$alkyl; or a radical -Alk-$R^7$, wherein Alk is $C_{1-4}$alkanediyl; and $R^7$ is hydrogen or hydroxy; Het is a heterocyclic radical of formula:

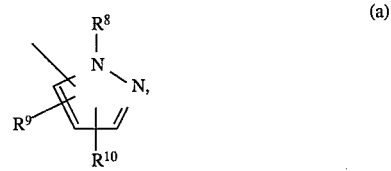

(a)

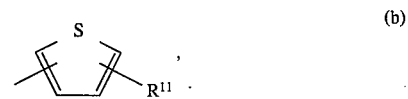

(b)

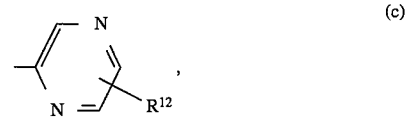

(c)

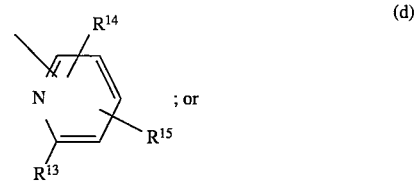

(d)

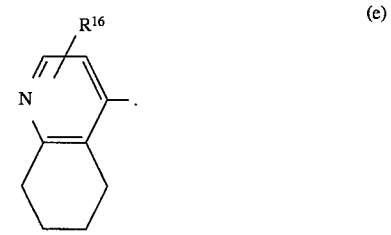

(e)

Pharmaceutical compositions containing said compounds of formula (I) and processes of preparing said compounds and compositions.

6 Claims, No Drawings

HETEROCYCLE-SUBSTITUTED BENZENEMETHANAMINE DERIVATIVES

CROSS-REFERENCE TO RELATED APPLICATIONS

This application is a divisional of application Ser. No. 08/240,737, filed May 12, 1994, now U.S. Pat. No. 5,480,997 is of PCT Application No. PCT/EP 92/02993, filed Dec. 22, 1992, published as WO93/13069, Jul. 8, 1993, which claims priority from EPO application Serial No. 91,203.431.1, filed Dec. 30, 1991.

BACKGROUND OF THE INVENTION

In U.S. Pat. No. 4,246,429 there are described a number of benzeneacetamides and thioamides being useful as intermediates in the preparation of phytopharmaceutical compounds. Unexpectedly, it has now been found that some analogous heterocyclic compounds effectively inhibit the replication of HIV and consequently may be useful for the treatment of individuals infected by HIV, in particular HIV-1.

DESCRIPTION OF THE INVENTION

The present invention is concerned with compounds having the formula

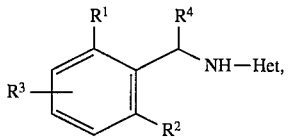

the pharmaceutically acceptable acid addition salt forms and the stereochemically isomeric forms thereof, wherein $R^1$ and $R^2$ each independently are halo or methyl;

$R^3$ is hydrogen, halo, nitro or trifluoromethyl;

$R^4$ is
  trifluoromethyl or methylcarbonyl; or
  a radical —C(=X)—NR$^5$R$^6$ wherein X is O or S, and $R^5$ and $R^6$ each independently are hydrogen or $C_{1-4}$alkyl; or
  a radical -Alk-R$^7$, wherein Alk is $C_{1-4}$alkanediyl; and $R^7$ is hydrogen or hydroxy;

Het is a heterocyclic radical of formula:

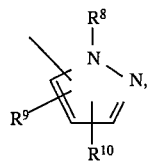

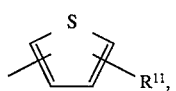

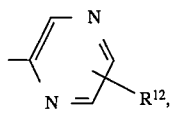

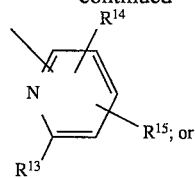

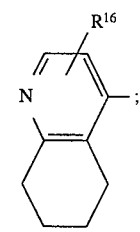

wherein $R^8$ is $C_{1-4}$alkyl or hydrogen;

$R^9$ and $R^{10}$ each independently are hydrogen, $C_{1-4}$alkylcarbonyl, $C_{1-4}$alkyl, halo or nitro;

$R^{11}$ is hydrogen, nitro, halo or $C_{1-4}$alkyl;

$R^{12}$ is hydrogen, $C_{1-4}$alkyl or $C_{1-4}$alkylcarbonyl;

$R^{13}$ is hydrogen or hydroxy;

$R^{14}$ is hydrogen, nitro, cyano, halo, $C_{1-4}$alkyl, $C_{1-4}$alkyloxy, $C_{1-4}$alkylcarbonyl;

$R^{15}$ is hydrogen, nitro, cyano, halo, $C_{1-4}$alkyl, $C_{1-4}$alkyloxy, $C_{1-4}$alkylcarbonyl; or $R^{14}$ and $R^{15}$ taken together form $C_{3-4}$alkanediyl;

$R^{16}$ is hydrogen, $C_{1-4}$alkylcarbonyl, nitro or halo; and in the heterocyclic radicals of formula (a), (c), (d) or (e) a nitrogen atom can optionally be oxidized.

The compounds of formula (I) wherein at least one of $R^5$ and $R^6$ is hydrogen or wherein $R^{13}$ is hydroxy may also exist in their tautomeric form. Said form, although not explicitly indicated hereinabove, is intended to be included within the scope of the present invention.

In the foregoing definitions and hereinafter the term halo defines fluoro, chloro, bromo and iodo; $C_{1-4}$alkyl defines straight and branched saturated hydrocarbon radicals having from 1 to 4 carbon atoms, such as, for example, .methyl, ethyl, propyl, 1-methylethyl, butyl, 1-methylpropyl, 2-methylpropyl and 1,1-dimethylethyl; $C_{1-4}$alkanediyl defines bivalent straight or branch chained hydrocarbon radicals containing from 1 to 4 carbon atoms such as, for example, 1,2-ethanediyl, 1,3-propanediyl, 1,4-butanediyl and the branched isomers thereof, $C_{3-4}$alkanediyl defines those $C_{1-4}$alkanediyl radicals which contain 3 or 4 carbon atoms such as 1,3-propanediyl or 1,4-butanediyl; $C_{1-4}$alkyloxy defines straight and branch chained alkyloxy radicals such as methoxy, ethoxy, propyloxy, butyloxy and the like; $C_{1-6}$alkyloxy defines said $C_{1-4}$alkyloxy radicals and the higher homologues thereof containing 5 or 6 carbonatoms, such as pentyloxy, hexyloxy; $C_{1-4}$alkylcarbonyl defines straight and branch chained acyl radicals such as methylcarbonyl, ethylcarbonyl, propylcarbonyl, butylcarbonyl and the like.

Pharmaceutically acceptable addition salts as mentioned hereinabove comprise the therapeutically active non-toxic addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term addition salt also comprises the hydrates and solvent addition forms which the compounds of formula (I) are able to form. Examples of such forms are e.g. hydrates, alcoholates and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms of the compounds of formula (I) are obviously intended to be embraced within the scope of this invention.

An interesting group of compounds are those compounds of formula (I) wherein $R^1$ and $R^2$ are halo; $R^3$ is hydrogen or halo; $R^4$ is a radical —C(=O)—$NR^5R^6$ or a radical -Alk-$R^7$, wherein $R^7$ is hydrogen.

More interesting compounds are those interesting compounds wherein Het is a heterocyclic radical
of formula (a), wherein
    $R^8$ is $C_{1-4}$alkyl;
    $R^9$ and $R^{10}$ each independently are $C_{1-4}$alkyl or nitro;
of formula (c), wherein
    $R^{12}$ is $C_{1-4}$alkylcarbonyl;
of formula (d), wherein
    $R^{13}$ is hydrogen or hydroxy;
    $R^{14}$ is hydrogen, nitro, cyano, $C_{1-4}$alkylcarbonyl;
    $R^{15}$ is hydrogen; or $R^{14}$ and $R^{15}$ taken together form $C_{3-4}$alkanediyl;
of formula (e), wherein
    $R^{16}$ is $C_{1-4}$alkylcarbonyl.

Particularly interesting compounds are those more interesting compound wherein $R^4$ is a radical C(=O)$NH_2$ or methyl and Het is 3-cyano-2-pyridinyl, 3-nitro-2-pyridinyl, 2-ethyl-5-methyl-4-nitro-2H-pyrazol-3-yl, 2-nitro-3-thienyl, 3-acetyl-5,6,7,8-tetrahydro-4-quinolinyl, 3-acetyl-2-pyridinyl, 3-acetyl-2-pyrazinyl, 1,2-dihydro-2-oxo-3-pyridinyl.

Preferred compounds are:
2,6-dichloro-α-[(3-cyano-2-pyridinyl)amino]benzeneacetamide,
2,6-dichloro-α-[(3-nitro-2-pyridinyl)amino]benzeneacetamide,
2,6-dichloro-α-[(2-ethyl-5-methyl-4-nitro-2H-pyrazol-3-yl)amino]benzeneacetamide,
1-[2-[[1-(2,6-dichlorophenyl)ethyl]amino]-3-pyridinyl]ethanone,
N-[1-(2,6-dichlorophenyl)ethyl]-3-nitro-2-pyridinamine,
2,6-dichloro-α-[(1,2-dihydro-2-oxo-3-pyridinyl)amino] benzeneacetamide,
α-[(3-acetyl-2-pyrazinyl)amino]-2,6-dichlorobenzeneacetamide,
1-[3-[[1-(2,6-dichlorophenyl)ethyl]amino]-2-pyrazinyl] ethanone, the pharmaceutically acceptable acid addition salt forms and the stereochemically isomeric forms thereof.

The compounds of formula (I) can be prepared by reacting an intermediate of formula (II) with an appropriate heterocyclic derivative of formula (III).

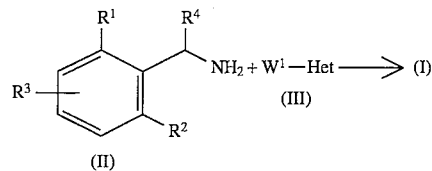

In formula (III), $W^1$ represents a reactive leaving group such as, for example, halo, preferably chloro or bromo; $C_{1-4}$alkyloxy; aryloxy; a sulfonyloxy group, e.g. methanesulfonyloxy, 4-methylbenzenesulfonyloxy and the like; or a $C_{1-6}$alkylthio. The reaction can be performed following art-known procedures, preferably at an elevated temperature and in particular at the reflux temperature of the reaction mixture, whereby an excess of one of the reactants can be used as solvent; or optionally in admixture with an appropriate solvent such as, for example, water, a dipolar aprotic solvent, e.g. N,N-dimethylacetamide; an ether, e.g. tetrahydrofuran; an alcohol, e.g. ethanol; an aromatic solvent, e.g. methylbenzene and the like and mixtures of such solvents. An appropriate base such as, for example, an alkali metal or an earth alkaline metal carbonate, hydrogen carbonate, hydroxide, alkoxide, hydride or amide, or an organic base such as, for example, an amine, e.g. N,N-diethylethanamine, N-(1-methylethyl)-2-propanamine, pyridine and the like, may optionally be used to pick up the acid which is formed during the course of the reaction. Additionally, it may be advantageous to conduct said reaction under an inert atmosphere such as, for example, oxygen-free argon or nitrogen gas. Phase transfer catalysis conditions may equally be employed in the above reaction.

In this and the following preparations, the reaction products may be isolated from the reaction mixture and, if necessary, further purified according to methodologies generally known in the art such as, for example, extraction, distillation, crystallization, trituration and chromatography.

The compounds of formula (I) can also be prepared by alkylating an appropriate heterocyclic derivative of formula (V) or a salt thereof, with an alkylating reagent of formula (IV) following art-known N-alkylation procedures. In formula (IV), $W^2$ represents a reactive leaving group such as, for example, halo, e.g. chloro, bromo or iodo, a sulfonyloxygroup, e.g. methanesulfonyloxy, 4-methylbenzenesulfonyloxy and the like reactive leaving groups.

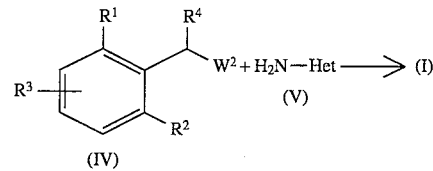

Said N-alkylation reaction can conveniently be carried out following art-known procedures by stirring the reactants in an appropriate solvent, optionally in admixture with a base.

The compounds of formula (I) wherein $R^4$ is a radical —C(=X)—$NR^5R^6$, wherein X is O or S, $R^5$ and $R^6$ are hydrogen; said compounds being represented by formula (I-a) when X is O and by formula (I-b) when X is S, can be prepared by reacting a nitrile of formula (VI), with a reagent $H_2X$ (VII), namely water or hydrogen suede, under appropriate conditions.

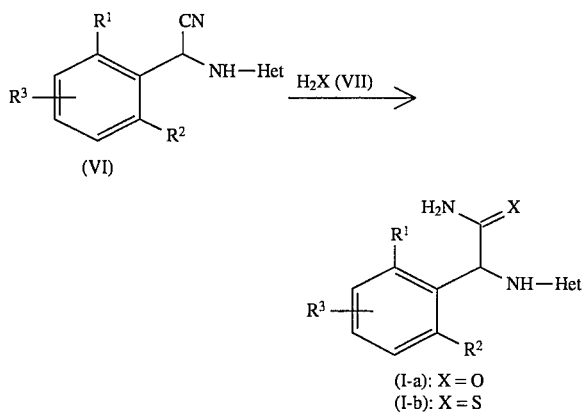

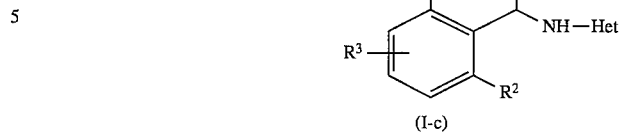

The hydrolysis of the nitrile (VI) to the corresponding amide (I-a), can easily be carried out following art-known procedures. Preferably said hydrolysis is carried out at room temperature or low temperatures such as, for example, between 0° C. and room temperature, in a concentrated strong acid, e.g. concentrated sulfuric acid, hydrochloric acid, hydrobromic acid and the like, optionally in the presence of a small amount of water. Alternatively the nitrile of formula (VI) can be hydrolyzed by stirring it in an appropriate solvent such as, for example, an alcohol, e.g. ethanol, in the presence of hydrogen peroxide and an appropriate base such as, for example, an alkali metal hydroxide, e.g. sodium hydroxide.

The nitrile (VI) can conveniently be converted into the thioamide (I-b) by reaction with hydrogen sulfide in an appropriate solvent, e.g. pyridine, a mono-, di- or trimethylated pyridine and the like solvents, and in the presence of an appropriate base such as an amine, e.g. N,N-diethylethanamine, N-methylmorpholine, N-(1-methylethyl)-1-methylethanamine and the like. This latter reaction can conveniently be conducted at room temperature and in some instances at lower temperatures such as, for example, between about 0° C. and room temperature. The thioamide compounds of formula (I-b) can conveniently be converted into the corresponding amides of formula (I-a) by reaction with an oxidizing reagent such as, for example, hydrogen peroxide in water, optionally in admixture with a reaction-inert organic co-solvent.

The compounds of formula (I) wherein $R^4$ is a radical —C(=O)—$NR^5R^6$, $R^5$ and $R^6$ each independently being hydrogen or $C_{1-4}$alkyl; said compounds being represented by formula (I-c), can be prepared by reacting an appropriate amine (IX) with an aminoacid or a derivative thereof, of formula (VIII), wherein L represents a leaving group such as, for example, hydroxy, $C_{1-6}$alkyloxy, 1-H-imidazolyl, $C_{1-6}$-alkyloxycarbonyl, phenoxycarbonyl or halo.

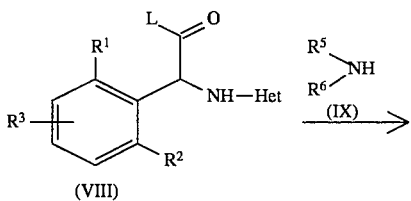

Said preparation of the amides of formula (I-c) can conveniently be carried out following art-known amidation and transamidation reactions. For example, said amides can be prepared by reacting an appropriate carboxylic acid (L is OH) with an amine (IX) in the presence of a reagent capable of promoting amidation reactions. Typical examples of such reagents are for example dicyclohexylcarbodiimide, 2-chloro-1-methylpyridinium iodide, phosphorus pentoxide, 1,1'-carbonylbis[1H-imidazole], 1,1'-sulfonylbis[1H-imidazole] and the like reagents.

Alternatively, said carboxylic acids may be converted into a suitable reactive functional derivative thereof such as, for example, an acyl halide, symmetric or mixed anhydride, ester, amide, acyl azide and the like derivatives, before reaction with the amine of formula (IX). Said reactive functional derivatives may be prepared following art known methods, for example, by reacting the carboxylic acid with a halogenating reagent such as, for example, thionyl chloride, phosphorous trichloride, polyphosphorous acid, phosphoryl chloride, oxalyl chloride and the like, or by reacting said carboxylic acid with an acyl halide such as acetyl chloride, ethyl chloroformate and the like. The compounds of formula (I) can also be converted into one another following art-known functional group transformation reactions. Thus, some compounds of formula (I) can also be useful as a precursor for other compounds of formula (I).

For example, the N-oxide forms of the compounds of formula (I) can conveniently be prepared by N-oxidation with an appropriate organic or inorganic peroxide such as, for example, hydrogen peroxide, perbenzoic acid, 3-chloroperbenzoic acid, tert. butyl hydroperoxide and the like. Suitable solvents of said N-oxidation reactions are, for example, water, alcohols, e.g. methanol, ethanol and the like, halogenated hydrocarbons, e.g. dichloromethane, trichloromethane and the like. The compounds of formula (I) wherein $R^5$ and $R^6$ are hydrogen can be converted into compounds of formula (I) wherein $R^5$ and/or $R^6$ are $C_{1-4}$alkyl by art-known alkylation procedures.

The compounds of this invention have at least one asymmetric carbon atom in their structure, namely the carbon atom bearing the $R^4$ group. Said chiral center and any other chiral center which may be present, can be indicated by the stereochemical descriptors R and S.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereospecific methods of preparation. These methods will advantageously employ enantiomerically pure starting materials. Stereochemically isomeric forms of the compounds of formula (I)

are obviously intended to be included within the scope of the invention.

The compounds of formula (I) as prepared in the above described processes are generally racemic mixtures of enantiomers which can be separated from one another following art-known resolution procedures. The racemic compounds of formula (I) which are sufficiently basic may be converted into the corresponding diastereomeric salt forms by reaction with a suitable chiral acid. Said diastereomeric salt forms are subsequently separated, for example, by selective or fractional crystallization and the enantiomers are liberated therefrom by alkaline or acidic hydrolysis.

An interesting manner of separating the enantiomeric forms of the compounds of formula (I) involves liquid chromatography using a chiral stationary phase such as suitably derivatized cellulose, for example, tri(dimethylcarbamoyl)cellulose (Chiracel OD®) and similar chiral stationary phases.

As an alternative to the above-mentioned resolution of the compounds of formula (I), there should be mentioned also the resolution of racemic intermediates. Particularly useful intermediates for this purpose are the aminoacid derivatives of formula (VIII), wherein L is hydroxy, said compounds being represented by formula (VIII-a).

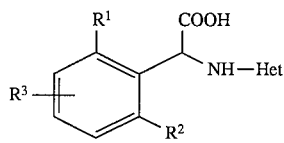

The aminoacids of formula (VIII-a) can conveniently be resolved by formation of the corresponding diastereomeric salt forms by reaction with a suitable chiral base such as chiral amines, e.g. α-methylbenzylamine, cinchonine and other alkaloid bases. Obviously, said aminoacids may also be resolved by liquid chromatography using an appropriate chiral stationary phase.

The enantiomeric forms of the aminoacids of formula (VIII-a) are converted into the enantiomeric forms of the compounds of formula (I-a) according to the procedures described hereinbefore for converting the intermediates of formula (VIII) into the compounds of formula (I).

A number of the intermediates and starting materials employed in the foregoing preparations are known compounds which can be prepared according to art-known methodologies of preparing said or similar compounds. Some intermediates are less common or are novel, and a number of preparation methods will therefore be described hereinafter in more detail.

The intermediates of formula (II), wherein $R^4$ is a radical —C(=X)—$NR^5R^6$ wherein X is O or S, $R^5$ and $R^6$ are hydrogen; said compounds being represented by (II-a) when X is O and by (II-b) when X is S, can be prepared by reacting the corresponding nitriles of formula (X), with a reagent $H_2X$ (VII), namely water or hydrogen sulfide, under appropriate conditions as described hereinabove for the formation of the compounds of formula (I-a) and (I-b).

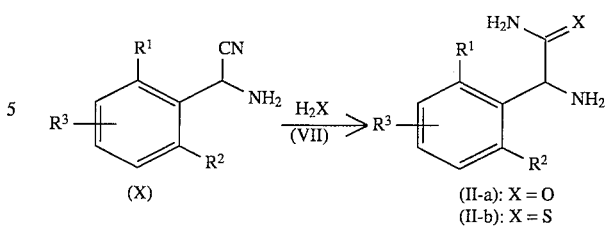

The nitriles of formula (X) can be prepared by reacting an appropriate benzaldehyde of formula (XI) with a cyanide salt, thus yielding the cyanohydrin of formula (XII), which is subsequently reacted with ammonia with formation of intermediates of formula (X). As examples of cyanide salts there may be mentioned alkali metal and earth alkaline metal cyanides, e.g. sodium and potassium cyanide. Suitable solvents comprise, for example, water, alcohols, e.g. methanol, ethanol and the like, carboxylic acids, e.g. acetic acid, particularly glacial acetic acid, propanoic acid and the like; or a mixture of such solvents. The intermediate cyanohydrin (XII) may be isolated or the reaction sequence may be performed as a one-pot procedure, for instance by reacting the benzaldehyde of formula (XI) with ammonium cyanide.

The intermediates of formula (VI), can be prepared by reacting an appropriate benzaldehyde (XI) with a heterocyclic amino derivative of formula (V) in the presence of a cyanide salt and a suitable solvent.

As examples of cyanide salts there may be mentioned alkali metal and earth alkaline metal cyanides, e.g., sodium and potassium cyanide. Suitable solvents comprise, for example, water; alcohols, e.g. methanol, ethanol and the like, carboxylic acids, e.g. acetic acid, particularly glacial acetic acid, propanoic acid and the like; or a mixture of such solvents. Said reaction is conveniently carried out by stirring at room temperature and, if desired, slightly heating the reactants, for example between 40° C. and 60° C., in particular at about 50° C. In some instances it is advantageous to carry out said reaction in the presence of a metal salt such as, for example, anhydrous zinc chloride and the like, in a non-aqueous solvent, particularly glacial acetic acid, as described in Chem. Ber., 98, 3902 (1965).

An interesting alternative to the latter formation of (VI) is condensing a benzaldehyde of formula (XI) with an amine of formula (V), thus forming an intermediate imine. Said imine can subsequently be treated with trimethylsilylcyanide in an appropriate solvent such as, for example, a halogenated hydrocarbon, e.g. trichloromethane, dichloromethane and the like, which yields the intermediate (VI) upon work-up.

The compounds of formula (I) show antiretroviral properties, in particular against Human Immunodeficiency Virus (HIV), also known as LAV, HTLV-III or ARV, which is the etiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

Due to their antiretroviral properties, particularly their anti-HIV properties, especially their anti-HIV-1-activity, the compounds of formula (I), their pharmaceutically acceptable salts and the stereochemically isomeric forms thereof, are useful in the treatment of individuals infected by HIV and for the prophylaxis of individuals. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

Additionaly, it has been found that also the intermediates of formula (VI) show antiretroviral properties, in particular against HIV and especially against HIV-1.

The subject compounds may be formulated into various pharmaceutical forms for administration purposes. As appropriate compositions there may be cited all compositions usually employed for systemically or topically administering drugs. To prepare the pharmaceutical compositions of this invention, an effective mount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. As appropriate compositions for topical application there may be cited all compositions usually employed for topically administering drugs, e.g., creams, jellies, dressings, shampoos, tinctures, pastes, ointments, salves, powders and the like. Application of said compositions may be by aerosol e.g. with a propellent such as nitrogen, carbon dioxide, a freon, or without a propellent such as a pump spray, drops, lotions, or a semisolid such as a thickened composition which can be applied by a swab. In particular compositions, semisolid compositions such as salves, creams, jellies, ointments and the like will conveniently be used.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

Those of skill in the treatment of HIV-infection could easily determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention.

Experimental part
A. Preparation of the intermediates
Example 1 a) To a stirred and cooled suspension of 438 g of 2,6-dichlorobenzaldehyde in 2000 g of glacial acetic acid there was added dropwise a solution of 203 g of potassium cyanide in 350 g of water, keeping the temperature below 25° C. Stirring was continued overnight at room temperature. The reaction mixture was concentrated and the residue, which solidified upon cooling, was filtered off and dried, yielding 438 g of (±)-2,6-dichloro-α-hydroxybenzeneacetonitrile; mp. 90° C. (interm. 1).

b) To a cooled (ice-bath) amount of 400 g of methanol saturated with $NH_3$ there were added 38 g of intermediate (1). The whole was stirred for 4 hours at reflux temperature and then left overnight to cool to room temperature. The reaction mixture was dried, filtered and evaporated. The residue was converted into the hydrochloride salt in 1,1'-oxybisethane by addition of 2-propanol saturated with HCl. The solvent was decanted and the oily residue was successively stirred in 1,1'-oxybisethane and in 2-propanone. The crystallized product was filtered off and dried, yielding 24.3 g of (±)-α-amino-2,6-dichlorobenzeneacetonitrile monohydrochloride; mp. >300° C. (interm. 2).

c) To a stirred and cooled amount of 450 g of concentrated sulfuric acid there were added 23 g of intermediate (2). Stirring was continued overnight at room temperature. The reaction mixture was poured into 2000 g of ice-water and the whole was basified with ammonia. The product was extracted with trichloromethane and the extract was dried, filtered and evaporated. The residue was crystallized from 240 g of 2-propanol at −20° C. The product was filtered off, washed with 2-propanol and petroleumether and dried, yielding 13.5 g of (±)-α-amino-2,6-dichlorobenzeneacetamide; mp. 166.3° C. (interm. 3).

Example 2

A mixture of 2,6-dichlorobenzaldehyde (0.012 mol) and 3-amino-2-pyridinone (0.01 mol) in acetic acid (50 ml) was stirred for 30 rain at room temperature. Potassium cyanide (0.012 mol) was added and the reaction mixture was stirred for 8 hours at room temperature. The reaction mixture was poured out into water (500 ml). The resulting precipitate was filtered off, washed with water and recrystallized from acetonitrile. The crystals were filtered off and dried, yielding: 1.1 g of (±)-2,6-dichloro-α-[(1,2-dihydro-2-oxo-3-pyridinyl)amino]benzeneacetonitrile (37.9%); mp. 213.3° C. (interm. 4).

B. Preparation of the final compounds
Example 3

A mixture of 2 g of intermediate (3), 1.74 g of 2-chloro-3-nitropyridine and a few drops of N,N-dimethylacetamide was stirred for ½ hour at 120° C. After cooling, the reaction mixture was purified by column chromatography (silica gel; $CH_2Cl_2/CH_3OH(NH_3)$ 97:3). The eluent of the desired fraction was evaporated and the residue was crystallized from acetonitrile. The product was filtered off and dried, yielding 0.8 g (25.5%) of (±)-2,6-dichloro-α-[(3-nitro-2-pyridinyl)amino]benzeneacetamide; mp. 207.2° C. (comp. 1).

Example 4

Intermediate (4) (0.007 mol) was dissolved in a mixture of ethanol (40 ml) and a sodium hydroxide solution 2N (10 ml). A solution of hydrogen peroxide solution 30% (3.5 ml) in ethanol (5 ml) was added dropwise at 5° C. The reaction mixture was stirred for 60 minutes at room temperature. The reaction mixture was extracted three times with $CH_2Cl_2$. The organic layer was separated, dried ($MgSO_4$), filtered and the solvent was evaporated. The residue was purified by column chromatography over silica gel (eluent: $CH_2Cl_2/(CH_3OH/H_3)$ 90/10). The pure fractions were collected and the solvent was evaporated. The residue was crystallized from 2-propanol. The crystals were filtered off and dried. Yielding: 1.1 g (±)-2,6-dichloro-α-[(1,2-dihydro-2-oxo-3-pyridinyl)amino]benzeneacetamide (27.5%). This fraction was recrystallized from $CH_3OH$. The crystals were filtered off and dried, yielding 0.24 g (±)-2,6-dichloro-α-[(1,2-dihydro-2-oxo-3-pyridinyl)amino]benzeneactetamide (11%)(comp. 8).

Example 5

A mixture of 2,6-dichloro-α-methylbenzenemethanamine (0.03 mol) and 2-chloro-3-pyridinecarbonitrile (0.03 mol) in N,N-dimethylacetamide (few drops) was stirred for 20 hours at 90° C. The reaction mixture was cooled and poured out into aqueous ammonia. The mixture was extracted twice with $CH_2Cl_2$. The organic layer was separated, washed with water, dried ($MgSO_4$), filtered and the solvent was evaporated. The residue was purified by column chromatography over silica gel (eluent: $CH_2Cl_2$/hexane 50/50). The pure fractions were collected and the solvent was evaporated, yielding 3.6 g (±)-2-[[1-(2,6-dichlorophenyl)ethyl]amino]-3-pyridinecarbonitrile (41.4%); mp. 84.4° C. (comp. 9).

Example 6

A mixture of 2,6-dichloro-α-methylbenzenemethanamine (0.01 mol) and 1-(2-chloro-3-pyridinyl)ethanone (0.01 mol) in a mixture of ethanol and water (1/1) (60 ml) was stirred in an autoclave for 18 hours at 150° C. The reaction mixture was cooled and diluted with water. This mixture was extracted twice with $CH_2Cl_2$. The organic layer was separated, washed with water, dried ($MgSO_4$), filtered and the solvent was evaporated. The residue was purified by column chromatography over silica gel (eluent: $CH_2Cl_2$/hexane 50/50). The pure fractions were collected and the solvent was evaporated. The residue (0.5 g) was crystallized from 2,2'-oxybispropane. The crystals were filtered off and dried. Yielding: 0.28 g (±)-1-[2-[[1-(2,6-dichlorophenyl)ethyl]amino]-3-pyridinyl]ethanone (9%); mp. 136.2° C. (comp. 11).

The following compounds of formula (l) were prepared:

TABLE 1

[Structure: 2,6-dichlorophenyl group with CH—NH—Het substituent and C=O-NH₂ group]

| Comp. no. | Ex. No. | —NH—Het | Physical data |
|---|---|---|---|
| 1 | 3 | —NH—(2-pyridinyl with NO₂ at 3-position) | 207.2° C. |
| 2 | 3 | —NH—(2-pyridinyl with CN at 3-position) | 212.2° C. |

TABLE 1-continued

Structure: 2,6-dichlorophenyl with CH(C(=O)NH₂)—NH—Het

| Comp. no. | Ex. No. | —NH—Het | Physical data |
|---|---|---|---|
| 3 | 3 | 5-amino-1-ethyl-4-nitro-3-methylpyrazol-5-yl-amino | 200.3° C. |
| 4 | 6 | 3-acetyl-5,6,7,8-tetrahydroquinolin-4-yl-amino | 233.9° C. |
| 5 | 3 | 2-nitrothiophen-3-yl-amino | 229.6° C. |
| 6 | 3 | 5-nitropyridin-2-yl-amino | 160.2° C. |
| 7 | 6 | 3-acetylpyrazin-2-yl-amino | 213.6° C. |
| 8 | 4 | 2-oxo-1,2-dihydropyridin-3-yl-amino | 251.9° C. |

TABLE 2

Structure: 2,6-dichlorophenyl with CH(R⁴)—NH—Het

| Comp. no. | Ex. No. | R⁴ | —NH—Het | Physical data |
|---|---|---|---|---|
| 9 | 5 | CH₃ | 3-cyanopyridin-2-yl-amino | 84.4° C. |
| 10 | 5 | CH₃ | 2-hydroxy-6,7-dihydro-5H-cyclopenta[b]pyridin-3-yl-amino | — |
| 11 | 6 | CH₃ | 3-acetylpyridin-2-yl-amino | 136.2° C. |
| 12 | 6 | CH₃ | 3-acetylpyrazin-2-yl-amino | 93.1° C. |
| 13 | 6 | CH₃ | 3-nitropyridin-2-yl-amino | 105.0° C. |
| 14 | 6 | CH₃ | 4-nitropyridin-3-yl-amino N-oxide | 155.0° C. |

C. Pharmacological example
Example 7

A rapid, sensitive and automated assay procedure was used for the in-vitro evaluation of anti-HIV agents. An HIV-1 transformed T4-cell line, MT-4, which was previously shown (Koyanagi et al., Int. J. Cancer, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in-situ reduction of 3-(4,5-dimethylthiazol-2-yl)-2,5-diphenyltetrazolium bromide (MTT). The 50% cytotoxic dose ($CD_{50}$ in μg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \quad \text{expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% effective dose ($ED_{50}$ in μg/ml). The ratio of $CD_{50}$ to $ED_{50}$ was defined as the selectivity index (SI). The compounds of formula (I) were shown to inhibit HIV-1 effectively. Particular values are listed in Table 1 hereinbelow.

TABLE 3

| Comp. No. | $CD_{50}$ (μg/ml) | $ED_{50}$ (μg/ml) | SI |
|---|---|---|---|
| 1 | 35.8 | 0.03 | 1299 |
| 2 | 25.3 | 0.10 | 243 |
| 3 | 121.8 | 2 | 61 |
| 8 | 217.2 | 0.18 | 1181 |
| 7 | 156.7 | 3.8 | 41.5 |
| 11 | 31.4 | 0.068 | 463 |
| 12 | 3.82 | 0.013 | 289 |
| 13 | 0.24 | 0.0073 | 33 |

D. Composition examples

"Active ingredient (A.I.) as used throughout these examples relates to a compound of formula (I) or (VI), a pharmaceutically acceptable acid addition salt or a stereochemically isomeric form thereof."

Example 8
Oral Drops

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I.. The resulting solution was filled into suitable containers.

Example 9
Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I.. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 10
Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient Example 11
Film-Coated Tablets
Preparation of tablet core A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 12
Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 l, giving a solution comprising 4 mg/ml of A.I.. The solution was sterilized by filtration (U.S.P. XVII p. 811 ) and filled in sterile containers.

Example 13
Suppositories

3 Grams A.I. was dissolved in a solution of 3 grams 2,3-dihydroxybutanedioic acid in 25 ml polyethylene glycol 400. 12 Grams surfactant (SPAN®) and triglycerides (Witepsol 555 ®) q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

Example 14
Injectable Solution

60 Grams of A.I. and 12 grams of benzylalcohol were mixed well and sesame oil was added q.s. ad 1 l, giving a solution comprising 60 mg/ml of A.I.. The solution was sterilized and filled in sterile containers.

Example 15

2% Cream 75 mg Stearyl alcohol, 20 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 20 mg of A.I. of formula (I), 1 mg polysorbate 80 and 637 mg purified water and a solution of 2 mg sodium sulfite anhydrous in purified water are next added to the emulsion while continuously mixing. The cream is homogenized and filled into suitable tubes.

Example 16

Aerosols a) To a solution of 2.5 mg A.I. in 0.7 ml of distilled water there are added 730 µg of a 0.1 N hydrochloric acid solution. After stirring for 10 minutes at room temperature, the pH of the thus obtained solution is adjusted to pH 5.5 by adding a 0.1N sodium hydroxide solution. Then there are added successively 4 mg of sodium chloride and 0.15 mg of phenylmercuric acetate and the whole is stirred to produce a complete solution. Distilled water is then added to a volume of 1.0 ml. The solution is filled in a glass bottle closed with a mechanical pump delivering 0.1 ml per puff upon administration.

b) To a solution of 2 mg A.I. in 0.7 ml of distilled water there are added 600 µg of a 0.1N hydrochloric acid solution. After stirring for 10 minutes at room temperature, 10 mg of polyvinylalcohol is dissolved in the mixture and the pH of the thus obtained solution is adjusted to pH 5.5 by adding a 0.1N sodium hydroxide solution. Then there are added successively 4 mg of sodium chloride and 2 mg of phenylethyl alcohol and the whole is stirred to produce a complete solution. Distilled water is added to produce a volume of 1.0 ml which is filled in a glass bottle closed with a mechanical pump spray delivering 0.1 ml per puff upon administration.

We claim:

1. A compound of the formula:

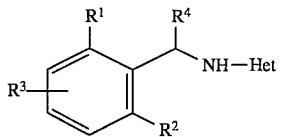
(I)

a pharmaceutically acceptable acid addition salt form or a stereochemically isomeric form thereof, wherein:

$R^1$ and $R^2$ each independently are halo or methyl;

$R^3$ is hydrogen, halo, nitro or trifluoromethyl;

$R^4$ is trifluoromethyl or methyl carbonyl; or a radical —C(=X)—NR$^5$R$^6$ wherein X is O or S, and $R^5$ and $R^6$ each independently are hydrogen or $C_{1-4}$alkyl; or a radical -Alk-R$^7$, wherein Alk is $C_{1-4}$alkanediyl; and $R^7$ is hydrogen or hydroxy; and Het is a heterocyclic radical of the formula:

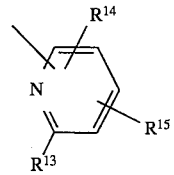
(d)

wherein:

$R^{14}$ and $R^{15}$ taken together form $C_{3-4}$alkanediyl, and $R^{13}$ is hydrogen or hydroxy, wherein in the heterocyclic radical (d), a nitrogen atom can optionally be oxidized, PROVIDED THAT when the heterocyclic radical (d) is a 5,6,7,8-tetrahydro-4-quinolinyl group, $R^{13}$ is hydroxy.

2. A compound according to claim 1 wherein $R^4$ is a radical C(C=O)NH$_2$ or methyl, and Het is 2-hydroxy-6,7-dihydro-5H-1-pyrindinyl.

3. A compound according to claim 2 wherein the compound is selected from the group consisting of:

3-[[1-(2,6-dichlorophenyl)ethyl]amino]-6,7-dihydro-5H-1-pyrindine-2-ol;

pharmaceutically acceptable salt forms thereof; and stereochemically isomeric forms thereof.

4. A pharmaceutical composition comprising a pharmaceutically acceptable carrier and as an active ingredient a therapeutically effective amount of a compound as defined in claim 1.

5. A pharmaceutical composition comprising a pharmaceutically acceptable carrier and as an active ingredient a therapeutically effective amount of a compound as defined in claim 2.

6. A pharmaceutical composition comprising a pharmaceutically acceptable carrier and as an active ingredient a therapeutically effective amount of a compound as defined in claim 3.

* * * * *